United States Patent
Lee et al.

(10) Patent No.: US 8,366,721 B2
(45) Date of Patent: Feb. 5, 2013

(54) POSITIONING DEVICE FOR SURGICAL OPERATION

(75) Inventors: Shih-Tseng Lee, Taoyuan County (TW); Wen-Yo Lee, Taoyuan County (TW); Heng-Liang Liu, Taoyuan County (TW)

(73) Assignee: Chang-Gung University (TW)

( * ) Notice: Subject to any disclaimer, the term of this patent is extended or adjusted under 35 U.S.C. 154(b) by 433 days.

(21) Appl. No.: 12/849,992

(22) Filed: Aug. 4, 2010

(65) Prior Publication Data

US 2011/0282355 A1  Nov. 17, 2011

(30) Foreign Application Priority Data

May 12, 2010  (TW) ............................. 99115203 A

(51) Int. Cl.
*A61B 19/00* (2006.01)
(52) U.S. Cl. .......................................... 606/130; 901/16
(58) Field of Classification Search .................. 606/130; 901/2, 14–16, 50
See application file for complete search history.

(56) References Cited

U.S. PATENT DOCUMENTS

| | | | | |
|---|---|---|---|---|
| 6,258,103 | B1 * | 7/2001 | Saracione | 606/130 |
| 6,684,129 | B2 * | 1/2004 | Salisbury et al. | 700/245 |
| 6,716,220 | B2 * | 4/2004 | Saracione | 606/130 |
| 7,763,015 | B2 * | 7/2010 | Cooper et al. | 606/1 |
| 8,048,088 | B2 * | 11/2011 | Green et al. | 606/130 |
| 8,083,753 | B2 * | 12/2011 | Solar et al. | 606/130 |
| 8,120,301 | B2 * | 2/2012 | Goldberg et al. | 318/581 |

* cited by examiner

*Primary Examiner* — Gary Jackson
*Assistant Examiner* — Eric Blatt
(74) *Attorney, Agent, or Firm* — Duane Morris LLP

(57) ABSTRACT

The primary objective of the present invention is to provide a positioning device for surgical operation, which could allow a surgical tool to be positioned precisely at a specific operating spot or a specific operating angle by providing a three axial free-moving function and a vertical and horizontal free-rotating function. Furthermore, the present invention is able to be electrically connected to and controlled by an automatic control system to achieve a more precise and efficient positioning function.

9 Claims, 3 Drawing Sheets

POSITIONING DEVICE FOR SURGICAL OPERATION

FIELD OF THE INVENTION

The present invention relates to a positioning device for surgical operation, and more particularly to a device, which could assist in precisely positioning a surgical tool at a fixed spot.

BACKGROUND OF THE INVENTION

With the progress of medical knowledge, many diseases and injuries in humans can be treated by surgical operation, such as excision, repair, etc.

However, in the medical field, there are numerous surgeries requiring precision to a certain extent, for example, a very small error in the width, depth, length, angle, etc. of an opening of an operating site in an affected part probably influences the success of a surgery. It is not easy to achieve high precision, error-free operation merely by human perception and judgment during a surgery. As we know, the precision of surgeries on many sites that are not clearly visible to the naked eye must be controlled based on doctors' experience. Unfortunately, in the current medical field, there are no instruments able to efficiently assist doctors in controlling the precision of surgeries during surgeries. Based on the consideration of the above-described circumstance, the inventors have speculated and designed a positioning device for surgical operation, which could solve the drawbacks of the existing techniques so as to improve the industrial applicability thereof.

SUMMARY OF THE INVENTION

In view of the above-mentioned problems of the prior art, the primary objective of the present invention is to provide a positioning device for surgical operation, which could overcome the difficulties of the existing techniques.

To achieve the foregoing objectives, the technical measures adopted by the invention include a positioning device for surgical operation comprising: a frame including a vertical frame body provided inside with a containing space; a transverse linear drive assembly correspondingly disposed in the containing space of the frame, which is an electronic device able to be controlled by a signal to move horizontally and linearly in a transverse direction selectively and which has a first rail member and a first drive member, wherein the first rail member is transversely and horizontally disposed on the frame and wherein the first drive member is correspondingly disposed on the first rail member and able to be driven by a first motor device to horizontally and linearly move in a transverse direction along the first rail member and wherein the first motor device may be electrically connected to an automatic control circuit; a vertical linear drive assembly correspondingly disposed on and interlocked with the first drive member, the vertical linear drive assembly being an electronic device able to be controlled by a signal to linearly move in a vertical direction selectively, which has a second rail member and a second drive member, the second rail member being correspondingly disposed vertical to the first drive member, wherein the second drive member is correspondingly disposed on the second rail member and able to be driven by a second motor device to vertically and linearly move along the second rail member and wherein the second motor device may be electrically connected to the automatic control circuit; a horizontal rotating drive assembly correspondingly disposed on and interlocked with the second drive member, the horizontal rotating drive assembly being an electronic device able to be controlled by a signal to selectively rotate in a horizontal direction, which has a first base and a first rotating member, the first base being correspondingly fixed on the second drive member, the first rotating member being correspondingly mounted on the first base and able to be driven by a third motor device to rotate in a horizontal direction relative to the first base and wherein the third motor device may be electrically connected to the automatic control circuit; a vertical rotating drive assembly correspondingly disposed on and interlocked with the first rotating member, the vertical rotating drive assembly being an electronic device able to be controlled by a signal to selectively rotate in a vertical direction, which has a second base and a second rotating member, the second base being correspondingly fixed on the first rotating member, the second rotating member being correspondingly mounted on the second base and able to be driven by a fourth motor device to rotate in a vertical direction relative to the second base and wherein the fourth motor device may be electrically connected to the automatic control circuit; a longitudinal linear drive assembly correspondingly disposed on and interlocked with the second rotating member, the longitudinal linear drive assembly being an electronic device able to be controlled by a signal to horizontally and linearly move in a longitudinal direction selectively, which has a third rail member and a third drive member, the third rail member being correspondingly and horizontally disposed longitudinal to the second rotating member, the third drive member being correspondingly disposed on the third rail member and able to be driven by a fifth motor device to horizontally and linearly move in a longitudinal direction along the third rail member, wherein the fifth motor device may be electrically connected to the automatic control circuit; and a surgical tool end correspondingly fixed on the third drive member and disposed thereon with a surgical tool, wherein the surgical tool may be a drilling tool, cutting tool or clamping tool for tool replacement as required by surgical operation.

Depending on the requirements of surgical operation, one surgical tool can be replaced with another surgical tool by the positioning device for surgical operation of the present invention, which could allow the surgical tool to be positioned precisely at a specific operating spot or a specific operating angle by providing a three axial free-moving function and a vertical and horizontal free-rotating function. Furthermore, the positioning device for surgical operation of the present invention can be electrically connected to and controlled by an automatic control system to achieve a more precise and efficient positioning function.

DETAILED DESCRIPTION OF THE PREFERRED EMBODIMENTS

The characteristics, contents, advantages and achieved effects of the present invention will become more fully understood from the detailed description given herein below and the accompanying drawings which are given by way of illustration only, and thus are not imitative of the present invention.

Figure 1:
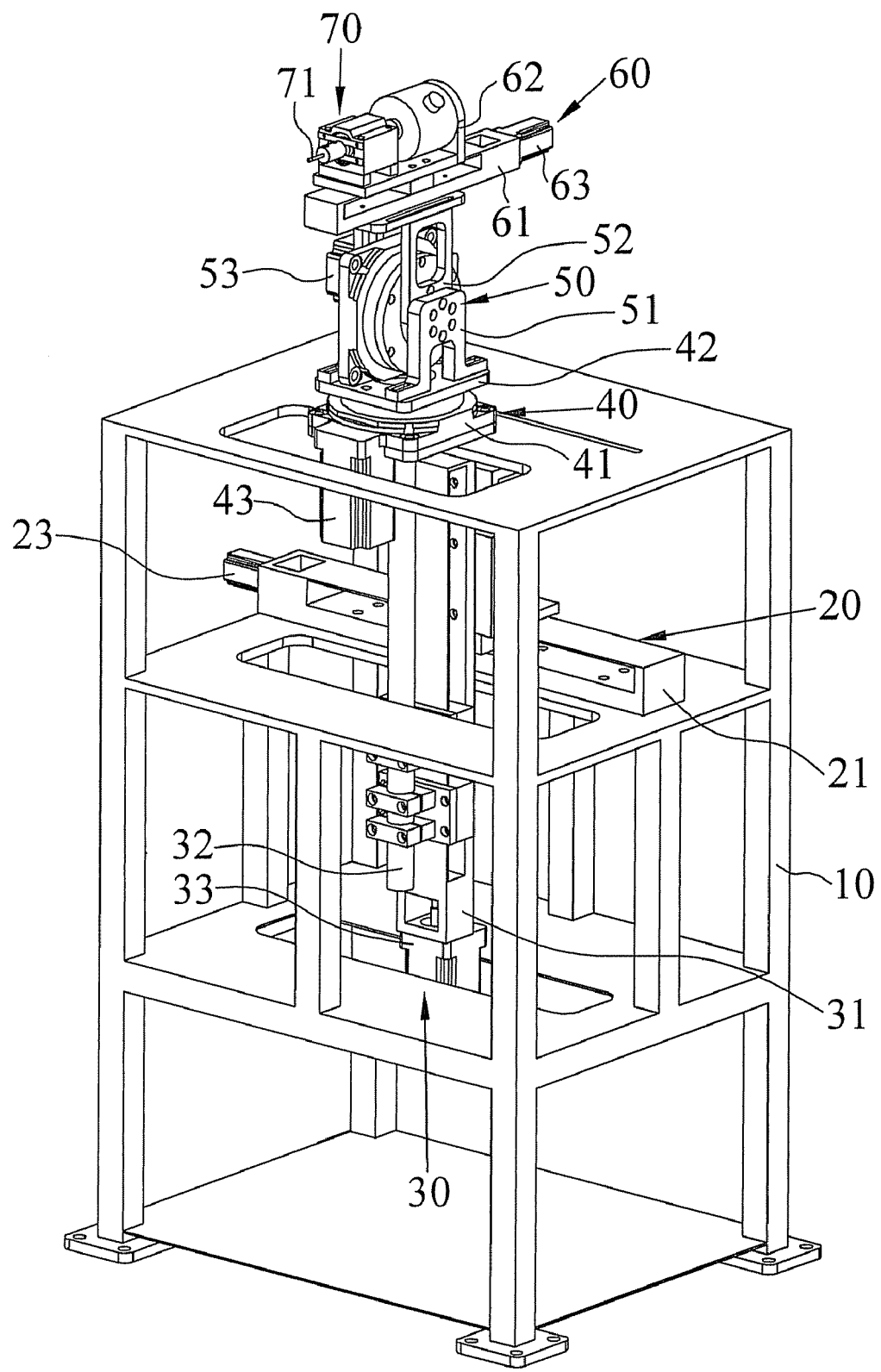
FIG. 1 is an appearance view of a positioning device for surgical operation according to the present invention.
Figure 2:
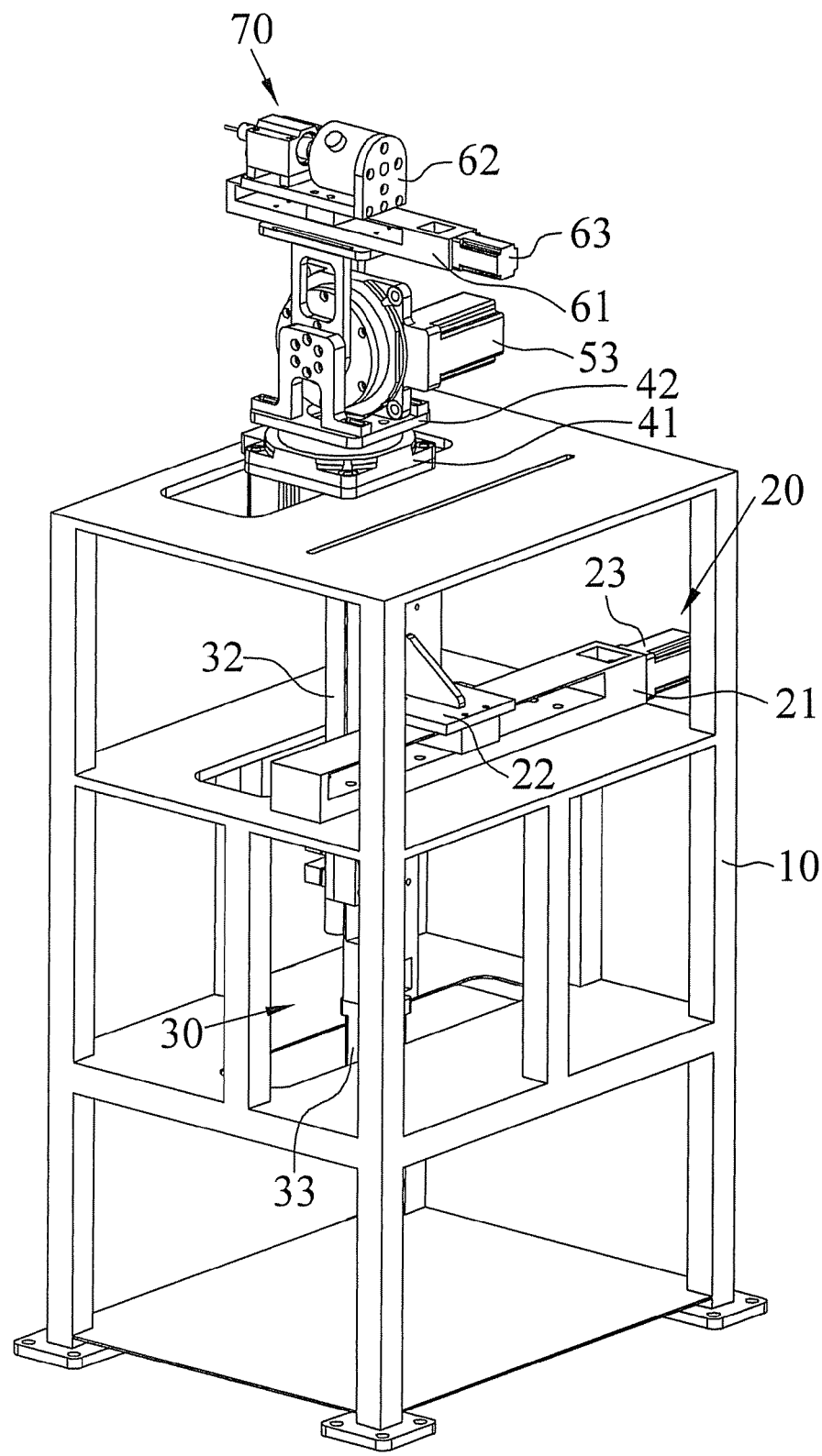
FIG. 2 is an appearance view from another viewing angle showing a positioning device for surgical operation according to the present invention.
Figure 3:
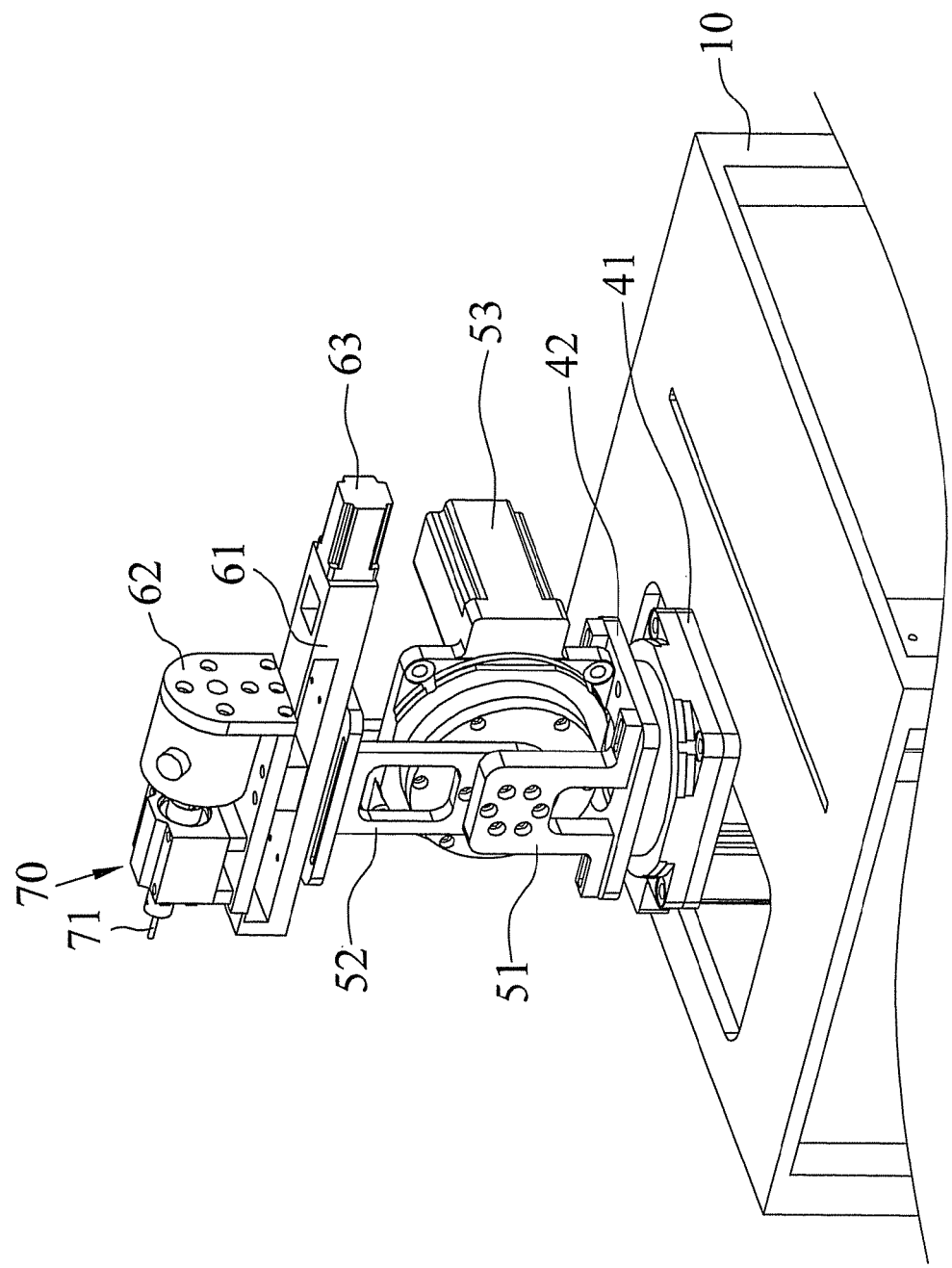
FIG. 3 is an appearance view of partial components in a positioning device for surgical operation according to the present invention.

Referring to FIGS. 1 to 3, the present invention relates to a positioning device for surgical operation, which in a preferred embodiment comprises a frame (10), a transverse linear drive assembly (20), a vertical linear drive assembly (30), a horizontal rotating drive assembly (40), a vertical rotating drive assembly (50), a longitudinal linear drive assembly (60) and a surgical tool end (70).

The above-mentioned frame (10) includes a vertical frame body provided inside with a containing space.

The above-mentioned transverse linear drive assembly (20) is correspondingly disposed in the containing space of the frame (10), which is an electronic device able to be controlled by a signal to move horizontally and linearly in a transverse direction selectively and which further comprises a first rail member (21) and a first drive member (22). The first rail member (21) is disposed transversely and horizontally on the frame (10). The first drive member (22) is movable, and correspondingly disposed on the first rail member (21) and able to be driven by a first motor device (23) to horizontally move horizontally and linearly in a transverse direction along the first rail member (21). The first motor device (23) may be electrically connected to an automatic control circuit.

The above-mentioned vertical linear drive assembly (30) is correspondingly disposed on and interlocked with the first drive member (22). The vertical linear drive assembly (30) is an electronic device able to be controlled by a signal to selective to linearly move in a vertical direction, which further comprises a second rail member (31) and a second drive member (32). The second rail member (31) is correspondingly disposed vertically to the first drive member (22). The second drive member (32) is disposed correspondingly and movably on the second rail member (31) and able to be driven by a second motor device (33) to move along the second rail member (31) vertically and linearly. The second motor device (33) may be electrically connected to the automatic control circuit.

The above-mentioned horizontal rotating drive assembly (40) is correspondingly disposed on and interlocked with the second drive member (32). The horizontal rotating drive assembly (40) is an electronic device able to be controlled by a signal to selectively rotate in a horizontal direction, which has a first base (41) and a first rotating member (42). The first base (41) is correspondingly fixed on the second drive member (32). The first rotating member (42) is rotatable, and mounted correspondingly on the first base (41) and able to be driven by a third motor device (43) to rotate in a horizontal direction relative to the first base (41). The third motor device (43) may be electrically connected to the automatic control circuit.

The above-mentioned vertical rotating drive assembly (50) is correspondingly disposed on and interlocked with the first rotating member (42). The vertical rotating drive assembly (50) is an electronic device able to be controlled by a signal to selectively rotate in a vertical direction, which has a second base (51) and a second rotating member (52). The second base (51) is correspondingly fixed on the first rotating member (42). The second rotating member (52) is rotatable, and correspondingly mounted on the second base (51) and able to be driven by a fourth motor device (53) to rotate in a vertical direction relative to the second base (51). The fourth motor device (53) may be electrically connected to the automatic control circuit.

The above-mentioned longitudinal linear drive assembly (60) is correspondingly disposed on and interlocked with the second rotating member (52). The longitudinal linear drive assembly (60) is an electronic device able to be controlled by a signal to move horizontally and linearly in a longitudinal direction selectively, which has a third rail member (61) and a third drive member (62). The third rail member (61) is longitudinal, and which is correspondingly and horizontally disposed to the second rotating member (52). The third drive member (62) is correspondingly and movably disposed on the third rail member (61) and able to be driven by a fifth motor device (63) to horizontally and linearly move in a longitudinal direction along the third rail member (61). The fifth motor device (63) may be electrically connected to the automatic control circuit.

The above-mentioned surgical tool end (70) is correspondingly fixed on the third drive member (62) and is disposed thereon with a surgical tool (71). The surgical tool (71) may be a drilling tool, cutting tool or clamping tool for tool replacement as required by surgical operation.

The positioning device for surgical operation ably designed by the present invention could allow the surgical tool end (70) to be positioned precisely at a specific operating spot or a specific operating angle by providing a three axial free-moving function and a vertical and horizontal free-rotating function. Furthermore, the positioning device for surgical operation of the present invention can be electrically connected to and controlled by an automatic control system to achieve a high degree of positioning precision that cannot be achieved by artificial surgical operation. For example, in an actual operation example, medical staff members can adjust the surgical tool end (70) to a spot or an angle to be surgically operated during the surgical operation by using the transverse linear drive assembly (20), the vertical linear drive assembly (30), the horizontal rotating drive assembly (40) and the vertical rotating drive assembly (50) followed by locking the movement of these four drive assemblies to achieve a reliable positioning function. Then, the longitudinal linear drive assembly (60) drives the surgical tool end (70) to linearly move in a single direction so as to assist in precise surgical operation. It is apparent that the present invention is a design with a high degree of freedom of manipulation and able to achieve rapid and precise positioning.

In summarization of the foregoing description, the present invention breaks through the prior art concept and indeed can achieve the effects to be improved, and it is also not easy for those skilled in the art to infer. Furthermore, the present invention is not known to the public prior to filing a patent application and meets the requirements of inventiveness and practical applicability of patents. Therefore, the application for a patent is duly filed accordingly.

The embodiments described above are only intended to illustrate the technical concepts and features of the present invention for those skilled in the art to understand the technical content of the present invention and to implement the present invention and are not intended to limit the scope thereof. Various changes or modifications can be made without departing from the spirit and scope of the invention. All such equivalent changes and modifications shall be included within the scope of the appended claims.

What is claimed is:

1. A positioning device, for surgical operation comprising:
a frame including a frame body provided inside with a containing space;
a transverse linear drive assembly correspondingly disposed in the containing space of the frame, the transverse linear drive assembly being an electronic device able to be controlled by a signal to move horizontally and linearly in a transverse direction selectively, the transverse linear drive assembly having a first rail member and a first drive member, wherein the first rail member is disposed transversely and horizontally on the frame and wherein the first drive member is correspondingly disposed on and able to move along the first rail member;

a vertical linear drive assembly correspondingly disposed on and interlocked with the first drive member, the vertical linear drive assembly being an electronic device able to be controlled by a signal to move linearly in a vertical direction selectively, the vertical linear drive assembly having a second rail member and a second drive member, the second rail member being disposed correspondingly and vertically to the first drive member, wherein the second drive member is correspondingly disposed on and able to move along the second rail member;

a horizontal rotating drive assembly correspondingly disposed on and interlocked with the second drive member, the horizontal rotating drive assembly being an electronic device able to be controlled by a signal to selectively rotate in a horizontal direction, the horizontal rotating drive assembly having a first base and a first rotating member, the first base being correspondingly fixed on the second drive member, the first rotating member being rotatable, and correspondingly mounted on the first base;

a vertical rotating drive assembly correspondingly disposed on and interlocked with the first rotating member, the vertical rotating drive assembly being an electronic device able to be controlled by a signal to selectively rotate in a vertical direction, the vertical rotating drive assembly having a second base and a second rotating member, the second base being correspondingly fixed on the first rotating member, the second rotating member being rotatable, and correspondingly mounted on the second base;

a longitudinal linear drive assembly correspondingly disposed on and interlocked with the second rotating member, the longitudinal linear drive assembly being an electronic device able to be controlled by a signal to move horizontally and linearly in a longitudinal direction selectively, the longitudinal linear drive assembly having a third rail member and a third drive member, the third rail member being horizontal and longitudinal, and disposed correspondingly to the second rotating member, the third drive member being correspondingly disposed on and able to move along the third rail member; and a surgical tool end correspondingly disposed on the third drive member.

2. The positioning device for surgical operation as set forth in claim 1, wherein the first drive member is able to be driven by a first motor device to linearly move along the first rail member; the second drive member is able to be driven by a second motor device to linearly move along the second rail member.

3. The positioning device for surgical operation as set forth in claim 2, wherein the first motor device and the second motor device are electrically connected to an automatic control circuit.

4. The positioning device for surgical operation as set forth in claim 1, wherein the first rotating member is able to be driven by a third motor device to rotate in a horizontal direction relative to the first base; the second rotating member is able to be driven by a fourth motor device to rotate in a vertical direction relative to the second base.

5. The positioning device for surgical operation as set forth in claim 4, wherein the third motor device and the fourth motor device are electrically connected to an automatic control circuit.

6. The positioning device for surgical operation as set forth in claim 1, wherein the third drive member is able to be driven by a fifth motor device to linearly move along the third rail member.

7. The positioning device for surgical operation as set forth in claim 6, wherein the fifth motor device is electrically connected to an automatic control circuit.

8. The positioning device for surgical operation as set forth in claim 1, wherein the surgical tool end is disposed thereon with a surgical tool.

9. The positioning device for surgical operation as set forth in claim 8, wherein the surgical tool is a drilling tool, cutting tool or clamping tool.

* * * * *